(12) United States Patent
Starta et al.

(10) Patent No.: US 8,785,857 B2
(45) Date of Patent: Jul. 22, 2014

(54) INFRARED SENSOR WITH MULTIPLE SOURCES FOR GAS MEASUREMENT

(75) Inventors: Christopher D. Starta, Pittsburgh, PA (US); Robert E. Uber, Pittsburgh, PA (US); Thomas Trautzsch, Cranberry Township, PA (US); Frederick J. Schuler, Wexford, PA (US)

(73) Assignee: MSA Technology, LLC, Cranberry Township, PA (US)

( * ) Notice: Subject to any disclaimer, the term of this patent is extended or adjusted under 35 U.S.C. 154(b) by 146 days.

(21) Appl. No.: 13/242,677

(22) Filed: Sep. 23, 2011

(65) Prior Publication Data

US 2013/0075615 A1   Mar. 28, 2013

(51) Int. Cl.
*G01J 5/02* (2006.01)

(52) U.S. Cl.
USPC ............................ 250/341.7; 356/51; 356/437

(58) Field of Classification Search
USPC ............... 250/341.7–341.8; 356/51, 437, 439
See application file for complete search history.

(56) References Cited

U.S. PATENT DOCUMENTS

| | | | |
|---|---|---|---|
| 3,614,431 A | 10/1971 | McHenry | |
| 4,355,234 A | 10/1982 | Fertig | |
| 4,560,875 A * | 12/1985 | Crowder | 250/343 |
| 4,598,201 A | 7/1986 | Fertig | |
| 4,902,896 A | 2/1990 | Fertig | |
| 5,464,983 A | 11/1995 | Wang | |
| 5,583,339 A * | 12/1996 | Black et al. | 250/339.13 |
| 5,693,944 A * | 12/1997 | Rich | 250/343 |
| 5,721,430 A * | 2/1998 | Wong | 250/339.13 |
| 5,726,752 A * | 3/1998 | Uno et al. | 356/246 |
| 5,734,165 A * | 3/1998 | Unal et al. | 250/338.1 |
| 5,923,035 A * | 7/1999 | Winkler et al. | 250/338.5 |
| 5,942,755 A | 8/1999 | Dreyer | |
| 6,067,840 A | 5/2000 | Chelvayohan | |
| 6,075,246 A | 6/2000 | Stock | |
| 6,114,700 A | 9/2000 | Blades | |
| 6,121,617 A * | 9/2000 | Hirayama et al. | 250/343 |
| 6,194,735 B1 * | 2/2001 | Martin | 250/573 |
| 6,255,653 B1 | 7/2001 | Kouznetsov | |
| 6,337,741 B1 | 1/2002 | Lind | |
| 6,370,940 B2 | 4/2002 | Warburton | |
| 6,392,234 B2 | 5/2002 | Diekmann | |
| 6,415,646 B1 | 7/2002 | Kessel | |
| 6,455,854 B1 | 9/2002 | Richman | |
| 6,509,567 B2 | 1/2003 | Boudet | |
| 6,538,251 B1 * | 3/2003 | Weckstrom et al. | 250/343 |

(Continued)

FOREIGN PATENT DOCUMENTS

DE   10202786 A1   8/2003
EP   0457624 A1   11/1991

(Continued)

*Primary Examiner* — David Porta
*Assistant Examiner* — Taeho Jo
(74) *Attorney, Agent, or Firm* — Bartony & Associates, LLC

(57) ABSTRACT

A closed path infrared sensor includes an enclosure, a first energy source within the enclosure, at least a second energy source within the enclosure, at least one detector system within the enclosure and a mirror system external to the enclosure and spaced from the enclosure. The mirror system reflects energy from the first energy source to the at least one detector system via a first analytical path and reflects energy from the second energy source to the at least one detector system via a second analytical path. Each of the first analytical path and the second analytical path are less than two feet in length.

20 Claims, 4 Drawing Sheets

(56) References Cited

U.S. PATENT DOCUMENTS

| | | |
|---|---|---|
| 6,573,521 B1 | 6/2003 | Lind |
| 6,583,417 B2 | 6/2003 | Stock |
| 6,670,613 B2 | 12/2003 | Prozzo |
| 6,670,887 B2 | 12/2003 | Dungan |
| 6,762,410 B1 * | 7/2004 | Wiechers et al. ............. 250/343 |
| 6,794,991 B2 | 9/2004 | Dungan |
| 6,818,895 B2 * | 11/2004 | Williams ...................... 250/343 |
| 6,918,281 B2 | 7/2005 | Sussman |
| 7,244,940 B2 | 7/2007 | Frodl |
| 7,329,870 B2 | 2/2008 | Wong |
| 7,332,719 B2 | 2/2008 | Frodl |
| 7,358,489 B2 | 4/2008 | Wong |
| 7,400,310 B2 | 7/2008 | LeMay |
| 7,432,508 B2 * | 10/2008 | Daniels et al. ................ 250/343 |
| 7,479,636 B2 * | 1/2009 | Scheying et al. ........ 250/339.06 |
| 8,097,856 B2 * | 1/2012 | Wong ........................... 250/345 |
| 8,253,942 B2 * | 8/2012 | Bristol ......................... 356/437 |
| 2001/0015408 A1 | 8/2001 | Stock |
| 2002/0036266 A1 | 3/2002 | Dreyer |
| 2002/0139934 A1 * | 10/2002 | Chang .......................... 250/343 |
| 2003/0147080 A1 | 8/2003 | Sarkis |
| 2005/0145796 A1 | 7/2005 | Davis |
| 2006/0226367 A1 * | 10/2006 | Hopkins et al. ............... 250/343 |
| 2007/0045542 A1 * | 3/2007 | Hashmonay ............. 250/339.12 |
| 2007/0267568 A1 | 11/2007 | Wolleswinkel |
| 2008/0106741 A1 | 5/2008 | Diekmann |
| 2010/0283991 A1 * | 11/2010 | Chrzan et al. .................. 356/51 |
| 2010/0302546 A1 | 12/2010 | Azimi |
| 2012/0091346 A1 * | 4/2012 | Bitter et al. ................ 250/341.7 |
| 2012/0194818 A1 * | 8/2012 | Disch ........................... 356/437 |

FOREIGN PATENT DOCUMENTS

| | | |
|---|---|---|
| GB | 2391310 A | 4/2004 |
| GB | 2442101 A | 3/2008 |
| GB | 2447535 B | 8/2011 |
| WO | WO2004031744 A1 | 4/2004 |
| WO | WO2005029048 A1 | 3/2005 |
| WO | WO2005111585 A2 | 11/2005 |

* cited by examiner

INFRARED SENSOR WITH MULTIPLE SOURCES FOR GAS MEASUREMENT

BACKGROUND

The following information is provided to assist the reader in understanding the technology described below and certain environments in which such technology can be used. The terms used herein are not intended to be limited to any particular narrow interpretation unless clearly stated otherwise in this document. References set forth herein may facilitate understanding of the technology or the background thereof. The disclosure of all references cited herein are incorporated by reference.

Infrared gas sensors use an energy source emitting infrared energy to detect the presence of an analyte in an environment being tested. In general, the analyte absorbs infrared energy of a certain wavelength and this absorption can be quantified to determine the concentration of the analyte in the test environment. Several embodiments of infrared fluid sensors or analyzers are discussed, for example, in U.S. Pat. Nos. 4,355, 234, 4,598,201 and 4,902,896, assigned to the assignee of the present invention, the disclosures of which are incorporated herein by reference.

Infrared (IR) gas detection instruments in, for example, the oil gas petrochemical or the "OGP" industry may use one or two infrared sources and one or two infrared detectors in the detection scheme. For those using two sources, one is used to directly measure gas in the analytical path. Those with a second source use it only internal to the instrument for purposes of stability, to compensate for unwanted internal analyte or to compensate for aging or degradation of components in the instrument. IR gas detection instruments with a second source typically use one of two common configurations. In the first configuration, a wide band source "A" is positioned to measure the transmission of a short path of internal housing atmosphere using two narrow band sensors at a reference and analytic waveband. Another wide band source "B" is positioned to measure the transmission of an external analytical path employing the same two narrow band detectors. The second configuration also uses two sources and two detectors. Unlike the first configuration, however, in the second configuration, the two sources are narrow banded at a reference waveband and at an analytic waveband.

These configurations attempt to manipulate the transfer function such that when the target transmission of the external path is calculated, certain parameters subject to variation, such as detector responsivity, may be cancelled. However, implementation is complex and expensive, and many problems still remain. For example, the transfer function for both configurations indicates that the total gas path is the product of the transmissions of the internal path and the external path. In the case in long term deployment, the internal path often becomes contaminated with either the target gas or an unknown analyte as a result of normal outgassing of materials within the housing. When this happens, the total transmission of the external-internal path changes, making it nearly impossible to provide a correct estimate of the concentration of an analyte in the external path.

SUMMARY

In one aspect, a closed path infrared sensor includes an enclosure, a first energy source within the enclosure, at least a second energy source within the enclosure, at least one detector system within the enclosure and a mirror system external to the enclosure and spaced from the enclosure. The mirror system reflects energy from the first energy source to the at least one detector system via a first analytical path and reflects energy from the second energy source to the at least one detector system via a second analytical path. In a number of embodiments, the first analytical path is different from the second analytical path. Each of the first analytical path and the second analytical path are less than two feet in length. Each of the first analytical path and the second analytical path may, for example, be less than one foot in length or less than six inches in length.

The mirror system may, for example, include a first mirror section having a concave shape over at least a portion of a surface thereof and a second mirror section having a concave shape over at least a portion of a surface thereof. The concave-shaped portion of the surface of the first mirror section and the concave-shaped portion of the surface of the second mirror section may intersect.

The first analytical path and the second analytical path may, for example, be of approximately the same length.

The first mirror section and the second mirror section may, for example, be formed on a monolithic or an integral base. In a number of embodiments, the base is formed (for example, monolithically) from a polymeric material upon which a reflective surface is supported.

The mirror system may, for example, be supported upon a mirror support that is spaced from the enclosure. In a number of embodiments, the mirror support is spaced from the enclosure by at least one extending member in operative connection with the enclosure.

The enclosure may, for example, include a window transmissive of infrared energy positioned between the first energy source, the second energy source, the at least one detector system and the mirror system. A length of the first analytical path within the enclosure may, for example, be less than 10% of a total length of the first analytical path. A length of the second analytical path within the enclosure may, for example, be less than 10% of a total length of the second analytical path. In a number of embodiments, the length of the first analytical path within the enclosure is less than 5% of a total length of the first analytical path, and the length of the second analytical path within the enclosure is less than 5% of a total length of the second analytical path.

The at least one detector system may, for example, be a multi-channel detector system including a housing and a beam splitter within housing. The multi-channel detector system may also include a reference channel and an analytical or sensing channel within the housing. The beam splitter may, for example, be adapted to split incident infrared light energy into two beams, wherein one beam is directed to a reference channel and another beam is directed to an analytical channel.

The first energy source and the second energy source may, for example, be modulated. The first energy source may, for example, be modulated at a first frequency, and the second energy source may, for example, be modulated at a second frequency different from the first frequency.

The mirror system may, for example, include a first mirror defining the first analytical path and a second mirror defining the second analytical path. The first mirror may, for example, be located at a first position and the second mirror may, for example, be located at a second position different from the first position so that a length of the first analytical path is different from a length of the second analytical path. Each of the first analytical path and the second analytical path may, for example, be less than one foot in length. Each of the first analytical path and the second analytical path may, for example, be less than six inches in length.

In another aspect, a method of detecting a gas includes exciting a first energy source positioned within an enclosure such that energy from the first energy source impinges upon a mirror system positioned external to the enclosure and spaced from the enclosure, the mirror system reflecting energy from the first energy source to at least one detector system positioned within the enclosure via a first analytical path; exciting at least a second energy source positioned within the enclosure such that energy from the second energy source impinges upon the mirror system, the mirror system reflecting energy from the second energy source to the at least one detector system via a second analytical path, which is different from the first analytical path, each of the first analytical path and the second analytical path being less than two feet in length; and determining a concentration of the gas based upon an analytical signal output from the detector system corresponding to the first analytical path and an analytical signal output from the detector system corresponding to the second analytical path.

In a further aspect, a mirror system includes a first mirror section having a concave shape over at least a portion of a surface thereof and a second mirror section having a concave shape over at least a portion of a surface thereof wherein the concave-shaped portion of the surface of the first mirror section and the concaved-shaped portion of the surface of the second mirror section intersect.

The technology described herein, along with the attributes and attendant advantages thereof, will best be appreciated and understood in view of the following detailed description taken in conjunction with the accompanying drawings.

DETAILED DESCRIPTION

As used herein and in the appended claims, the singular forms "a," "an", and "the" include plural references unless the context clearly dictates otherwise. Thus, for example, reference to "a mirror system" includes a plurality of such mirror systems and equivalents thereof known to those skilled in the art, and so forth, and reference to "the mirror system" is a reference to one or more such mirror systems and equivalents thereof known to those skilled in the art, and so forth.

In a number of embodiments, the sensors hereof are closed path or short path systems (sometimes referred to as point detectors) wherein, for example, the analytical paths are relatively short as compared to open path or long path systems. Open path systems can, for example, have analytical paths that extend many feet, indeed even hundreds of feet or more. Closed path system have analytical paths that are usually less than two feet, often less than one foot or even less than six inches.

Figure 1:
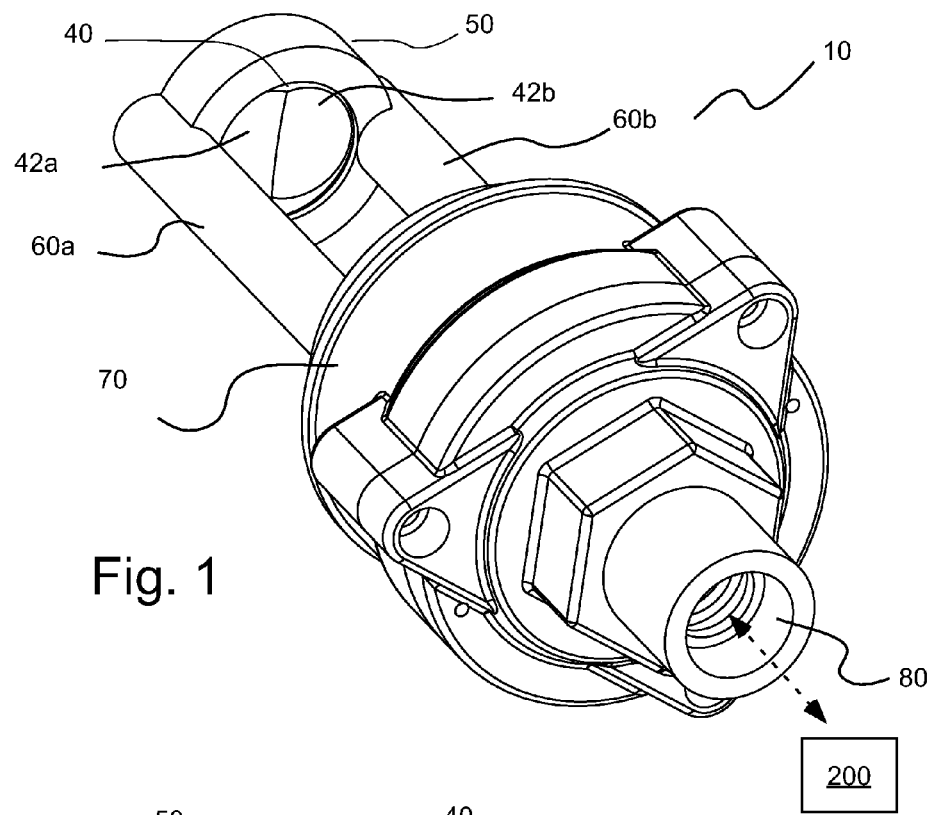
FIG. 1 a perspective view of an embodiment of an infrared gas sensor.
Figure 2:
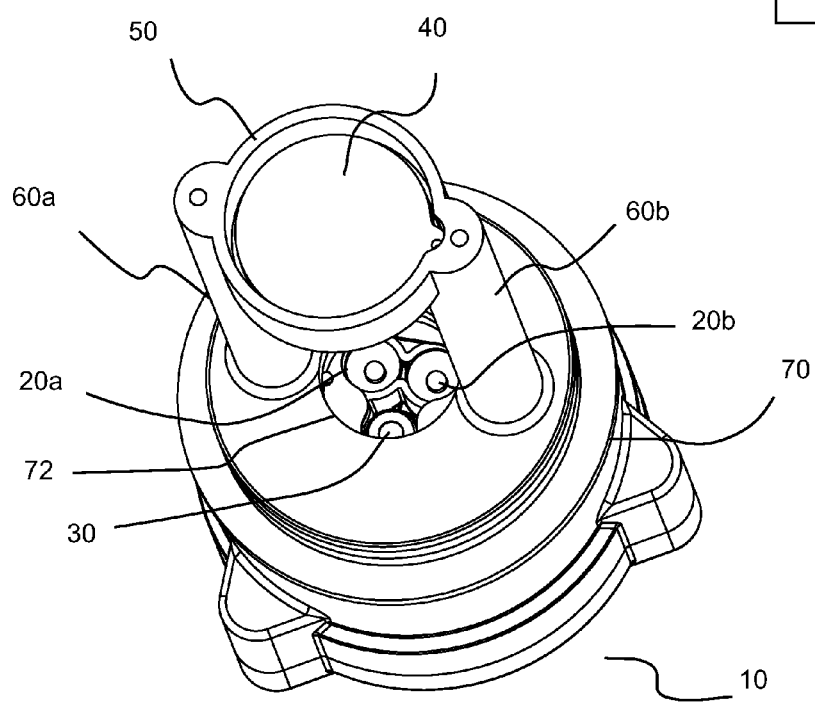
FIG. 2 illustrates another perspective view of the sensor of FIG. 1.

FIGS. 1 and 2 illustrate an embodiment of an infrared gas sensor 10 including a first energy source 20a and at least a second energy source 20b. In the illustrated embodiment, one detector system 30 is provided to quantify absorption that occurs along the analytical path of each of energy sources 20a and 20b. Energy sources 20a and 20b may, for example, be modulated to enable use of single detector system 30 wherein energy delivered to detector system 30 from energy sources 20a and 20b is, for example, separated in time. Alternatively, a separate detector system may be provided for each energy source.

In a number of embodiments, energy sources 20a and 20b are light sources. Sensor 10 further includes a mirror system 40 spaced from light sources 20a and 20b and from detector system 30. The transmission of energy from light sources 20a and 20b to mirror system 40 and reflection back to detector system 30 defines the analytical path associated with each light source 20a and 20b. In the embodiment of FIGS. 1 and 2, mirror system 40 includes two concave mirror sections 42a and 42b formed as a generally integral complex mirror surface as illustrated, for example, in FIGS. 1 and 3.

Figure 3:
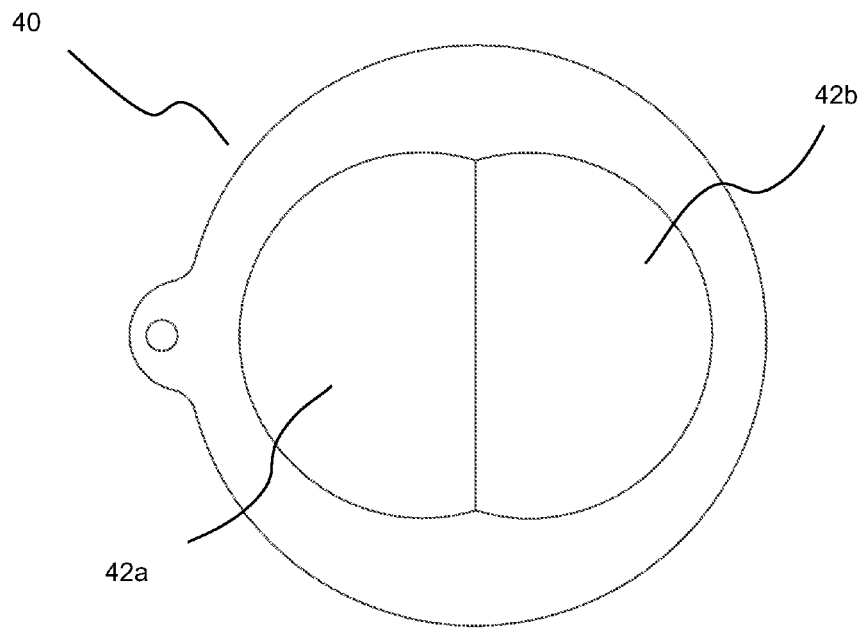
FIG. 3 illustrates an enlarged plan view of an embodiment of a complex mirror for use in the sensor of FIG. 1.
Figure 4:
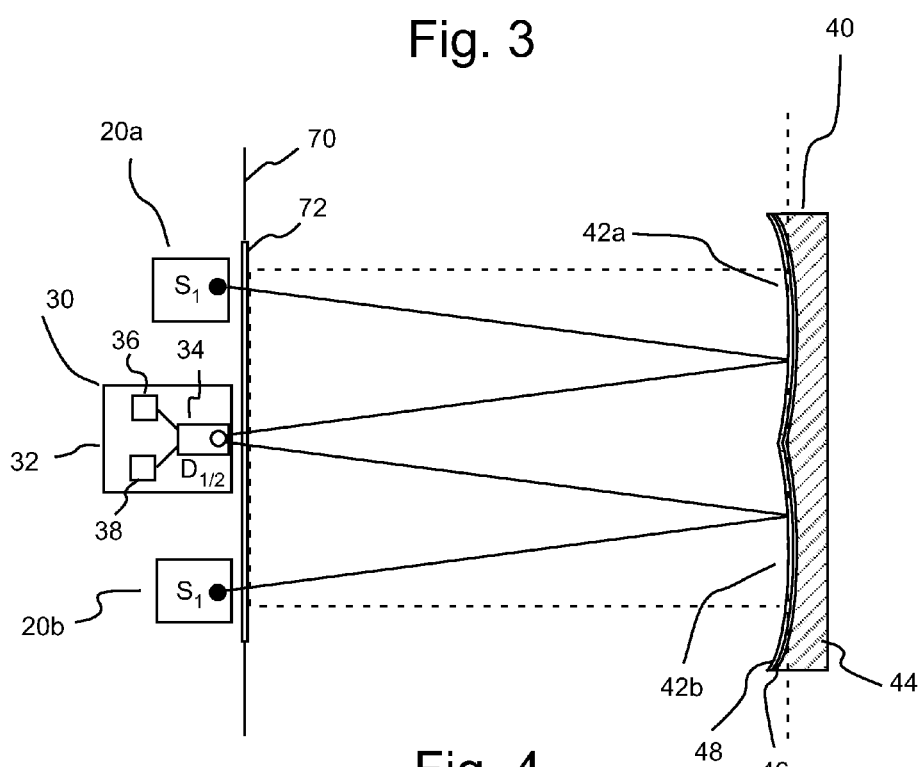
FIG. 4 illustrates schematically the detection or analytical paths of the energy sources of the sensor of FIG. 1 for use with a detector system.

In several embodiments, a polymeric element including the complex shape illustrated in FIGS. 1 and 3 wherein two concave sections or regions intersect is used as a base in mirror system 40. The base or support in which the intersecting concave regions were formed was, for example, coated with a reflective surface to form mirror system 40. Formation of mirror sections 42a and 42b as described above is relatively inexpensive. Further concave mirrors provide an improved signal as compared to generally flat mirrors. In a number of embodiments mirror system 40 was created by forming a base 44 from a polymeric material such as a cyclo-olefin polymer as illustrated schematically, for example, in FIG. 4. An aluminized, reflective coating 46 was then vapor deposited upon base 44. Subsequently, a protective coating 48 such as an $SiO_2$ coating was deposited upon reflective coating 46.

In general, the greater the length of the analytical path associated with light sources 20a and 20b, the greater the absorption that can occur in the presence of an analyte gas or gases. However, more scattering can occur as the analytical path length is increased. There is a balance or an optimization with respect to the distance mirror system 40 is positioned from light sources 20a and 20b and from detector system 30. Use of concave mirror sections 42a and 42b may, for example, assist in enabling an increase in the analytical path length.

In the illustrated embodiment, mirror system 40 is supported by a mirror support 50. In the illustrated embodiment, mirror support 50 (and thereby mirror system 40) is spaced from an enclosure, sensor housing or base 70 via extending support members 60a and 60b. Energy sources 20a and 20b, as well as detector system 30, are positioned within enclosure or housing 70, aligned with a port or window 72 formed in enclosure or housing 70. The length of extending support members 60a and 60b defines the length of the analytical paths of energy sources 20a and 20b.

In a number of embodiments, tungsten lamps which emit light energy over a range of wavelengths including the analytical wavelengths (over which the analyte absorbs energy) as well as in the visible spectrum were used for energy sources 20a and 20b. Tungsten lamps are relatively inexpensive and emission in the visible spectrum provides observable evidence (via window 72) that energy sources 20a and 20b are operational.

Figure 5A:
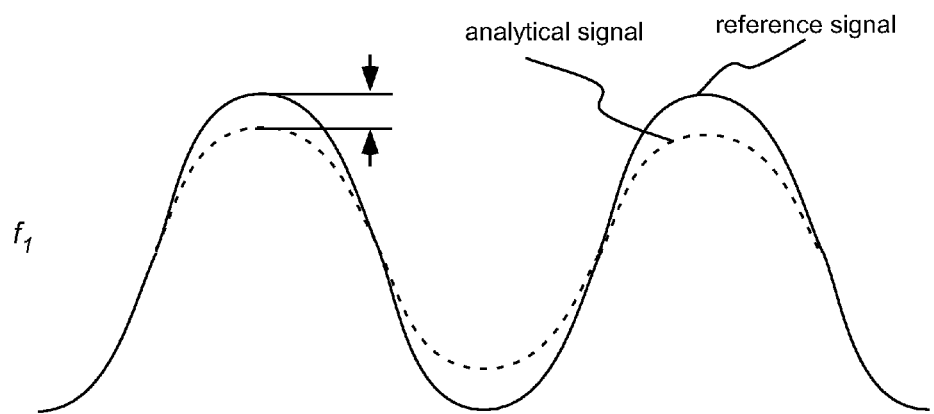
FIG. 5A illustrates a measured signal from one energy source operated at a first frequency $f_{-1}$.
Figure 5B:
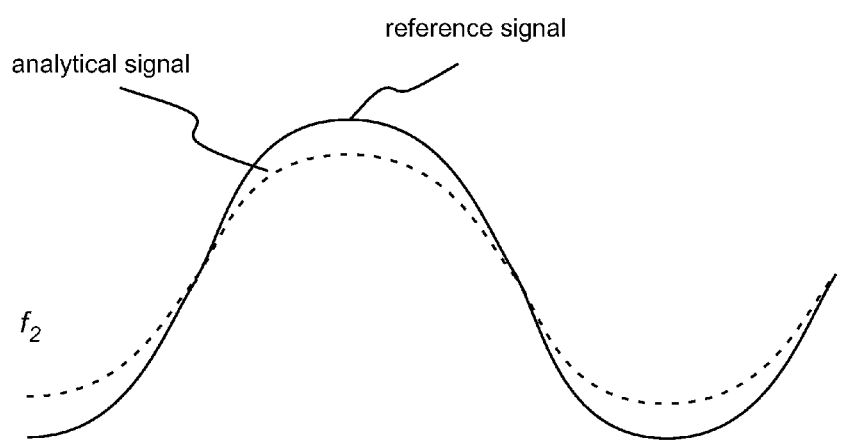
FIG. 5B illustrates a measured signal from another energy source operated at a second frequency $f_{-2}$, different from the first frequency $f_{-1}$ of FIG. 5A.

FIG. 5A illustrates an output signal from detector system 30 for energy source 20a. In the illustrated embodiment, energy source 20a is modulated at a first frequency $f_1$. The change in the measured signal resulting from the presence of an analyte gas is illustrated with a dashed line in FIG. 5A (analytical signal), while the reference signal is illustrated with a solid line. FIG. 5B illustrates an output signal from detector system 30 for energy source 20b. In the illustrated embodiment, energy source 20b is modulated at a second frequency $f_2$. Similar to FIG. 5A, the change in the measured signal resulting from the presence of an analyte gas is illustrated with a dashed line in FIG. 5B (analytical signal), while the reference signal is illustrated with a solid line. In a number of embodiments, energy source 20a was modulated at a different frequency $f_1$ (for example, 3 Hz) than frequency $f_2$ (for example, 5 Hz) at which energy source 20b was modulated. It was found that modulation of the energy sources at different frequencies resulted in signals well adapted for characterization or analysis via, for example, a Fourier transform algorithm.

In a number of embodiments, energy sources 20a and 20b were energized on and off at different frequencies as described above (for example, at 3 Hz and 5 Hz, respectively). In a number of embodiments, the method of controlling the duty cycle of energy sources 20a and 20b included creating an overall sample rate for digitizing the signals from each of the two receiving channels (that is, the reference and analytic receiving channels) of detector system 30. In that regard, in a number of embodiments, detector system 30 was a multi-channel (for example, a dual-channel) detector system including a housing 32 and a beam splitter 34 within housing 32 (see FIG. 4). Beam splitter 34 splits the incident energy/infrared light energy into two beams which are directed to a reference channel 36 and to an analytical channel 38. The created sample rate was also used to control the on-off modulation of each of energy sources 20a and 20b. By using this technique, the energy source drive, the received signal and the demodulation were held "locked" while rejecting unwanted noise. The amplitude of the received waveform was extracted by, for example, first generating sine and cosine values for each sample time. The value of the sine and cosine at each sample was multiplied by the corresponding amplitude of the received signal using the corresponding frequency to be demodulated. The result of this product included the original signals plus the sum and difference. By integrating over the period, a filter was created that filters out all but the difference component. These calculations were carried out for each receiving channel 36 and 38 to generate a ratio of reference to analytic that was indicative of the detected signal. The calculation was performed at each specific frequency to produce two independent signals.

In a number of embodiments the energizing (modulation) of the sources 20a and 20b is separated in time. This simple scheme allows for simple modulation of both sources to be identical. In such embodiments, demodulation is simply based on the peak value of the received waveform. This modulation scheme also eliminates crosstalk from one source to the other. In a representative example, first source 20a is modulated for 5 seconds, and the reception of its energy is processed. Source 20b is then modulated for 5 seconds, and the reception of its energy is then processed. Separation of the modulation of sources 20a and 20b in time may also permit changes in the modulation frequency over time. For example sources 20a and 20b may be modulated at a 5 hz rate for a period of 20 seconds, wherein first source 20a is modulated for the first 10 seconds and then second source 20b is modulated for the next ten seconds. The modulation rate for each of source 20a and 20b may, for example, then be changed to a 10 hz rate for the next 20 seconds. For each of source 20a and 20b, the incident infrared energy is split into two beams which are directed to a reference channel 36 and to an analytic channel 38.

In a number of embodiments the modulation of sources 20a and 20b may be continuous in time and separated in frequency. Digital Fourier techniques may be applied to extract the reception of two separate pairs of reference and analytic signals from reference channel/detector 36 and analytic channel/detector 38. This type of modulation permits fast time response to a step change of target gas in the external gas path. In this type of modulation, increasing the rate at which the received signals are sampled has the effect of increasing the resolution. The sample rate may also be used as a time tick to signal when the sources 20a and 20b are turned on and off (modulated). Therefore, the modulation and reception may be said to be "phase locked" or "frequency locked". The bandwidth of a phase locked system may be very narrow, allowing for maximum noise rejection.

Components within enclosure or housing 70 may, for example, be placed in communication with a power and/or control system or systems 200 via a passage 80 as illustrated in FIG. 1.

A number of currently available infrared sensors include a light source and an associated detector system measuring a light path/volume which is internal to the sensor housing, which is used for comparison to a light source/detector pair having an analytical path external to the housing to detect an analyte. The internal light source can be used for comparison or compensation. Use of such an internal light source can, for example, be used to detect deterioration in the analytical light source and/or to normalize a signal resulting from the analytical light source. Moreover, analyte gas can sometimes enter within the enclosure or housing of the sensor. An internal light source/detector pair can compensate for such gas within the sensor enclosure.

In a number of embodiments, the path of the light energy from energy sources 20a and 20b and to detector system 30 within enclosure or housing 70 is reduced or minimized with respect to the path outside enclosure or housing 70. For example, the distance between energy sources 20a and 20b and window 72 (for example, a sapphire or other window which is transmissive of infrared light) may be reduced or minimized and the distance between detector system 30 and window 72 may be reduced or minimized. The need for an internal light source for compensation is thereby reduced or minimized. Thus, in a number of embodiments of sensors hereof, no light source/detector pair internal to enclosure or housing 70 is present. In several embodiments, the internal path lengths associated with each energy source 20a and 20b (that is, the internal distance along the light path from energy source 20a/20b to window 72 plus the distance along the light path from the window 72 to detector system 30) of the infrared light energy was no more than 10% of the total path length associated with each energy source 20a and 20b (that is, the total distance along the light path from energy source 20a/20b to mirror section 42a/42b plus the distance along the light path from mirror section 42a/42b to detector system 30) or even no more than 5% of the total path length. In one representative embodiment, for example, the internal path length was 0.23 inches and the external path length 5.98 inches. Thus the internal path length was 3.7% of the total path length ((0.23/(0.23+5.98))×100%=3.7%).

As described above, multiple light sources are used to create a redundant measurement through an analytical volume in several embodiments of sensors hereof, thereby improving instrument reliability. Reliability is, for example, a very important requirement in the OGP industry. Any improvement in the reliability of such gas detection instruments can, for example, increase safety and reduce factory down-time, thereby providing utility to the end user. Sensors using a single source for analytical measurement are statistically more likely to encounter a debilitating sensor failure than sensors using multiple or redundant sources for analytical measurement. In a number of embodiments hereof wherein both analytical light source were active, the measured output from the analytical light sources hereof was averaged to obtain an accurate reading.

Figure 6:
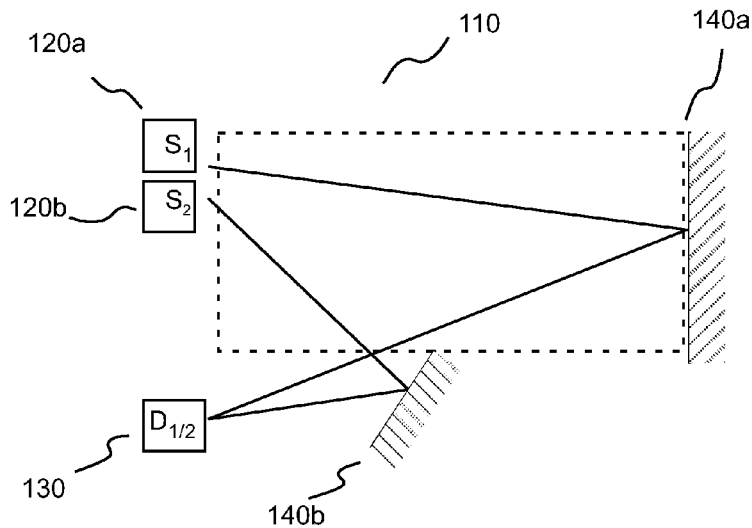
FIG. 6 illustrates schematically another embodiment of the analytical paths for two energy sources for use with a single detector system wherein the path length for each energy source is different.
Figure 7:
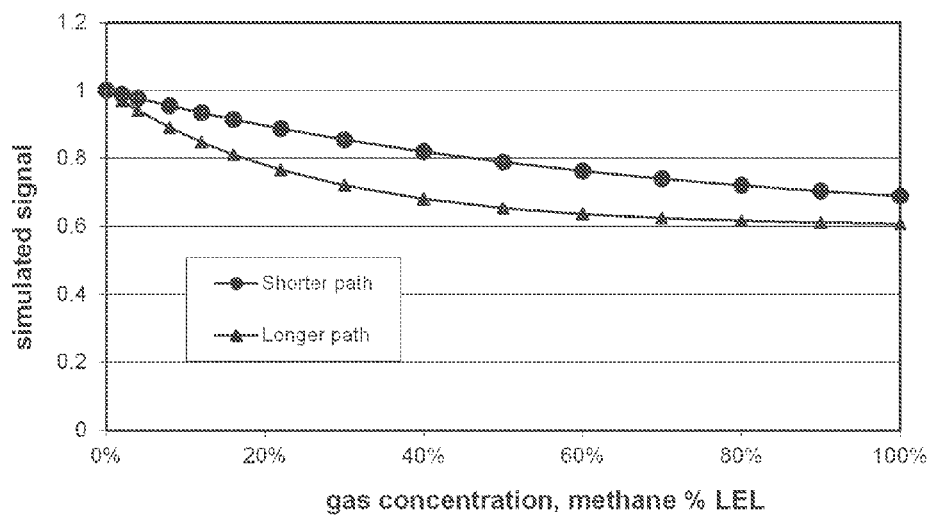
FIG. 7 illustrates a graph of simulated signal as a function of methane concentration (set forth as a percent of lower explosion level or % LEL) for a sensor having two analytical paths of different lengths.

In the embodiments described in connection with FIGS. 1 through 4, the analytical path length of light sources 20a and 20b was the same or approximately the same (for example, within 0 to 5%). As illustrated in FIG. 6, a sensor 110 may, for example, include two light sources 120a and 120b and a detector system 130. Two mirrors 140a and 140b are positioned at different positions such that the analytical path lengths associated with each of light sources 120a and 120b are different. Use of different analytical path lengths may, for example, enable the detection of different analyte gases and/or different concentration ranges for a particular analyte gas. The signal from the different analytical path lengths may be combined in several manners to determine a single gas concentration reading. For example, in FIG. 7 (setting for a study of simulated signal as a function of methane concentration (% LEL)), at low gas concentrations), the longer length analytical path provides a greater reduction in the optical signal (or exhibits a steeper slope) and thus provides a greater signal-to-noise ratio than the shorter length analytical path. At higher gas concentrations, however, the shorter length analytical path provides a greater reduction in the optical signal (or exhibits a steeper slope) and thus provides a greater signal-to-noise ratio for gas concentration changes than the longer length analytical path. Thus for a single gas reading, the weighted contribution of each analytical path could be adjusted based on the path length differences or on signal-to-noise ratios of the path lengths at the measured gas concentration. Other algorithms known to those skilled in the art may be used for combining the two different analytical path length signals into one gas reading.

In a number of embodiments, the position of for example, mirrors 42a and 42b, mirrors 140a and 140b, or other mirrors of sensors or systems hereof relative to one or more detector systems hereof is movable to adjust the length of the analytical paths. In the case of a sensor with separate mirror systems, the positions of the separate mirrors may be adjustable independently. A manufacturer may, for example, adjust the position of the mirrors) during manufacture to "tune" a sensor to specific requirements of an end user (for example, detection of one or more specific analyte gases). The position of one or more mirrors of a sensor may, for example, be adjusted using cooperating threading, via a telescoping member equipped with locking set screws and/or via other mechanisms know in the mechanical arts. In the embodiment of sensor 10, for example, the length of extending support members 60a and 60b may be adjustable as described above. In a number of embodiments, the position of one or more mirrors relative to the position of one or more detector systems of a sensor hereof can be changed during use to adjust the length of associated analytical paths. For example, the position of a mirror relative to a detector system can be varied continuously or discontinuously over time to sweep through a range of path lengths. An actuator such as a motor, a piezoelectric actuator, etc. may, for example, be used to effect change in the position of a mirror relative to an associated detector.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A closed path infrared sensor, comprising:
an enclosure,
a first energy source within the enclosure,
at least a second energy source with the enclosure,
at least one detector system within the enclosure, and
a mirror system external to the enclosure and spaced from the enclosure, the mirror system reflecting energy from the first energy source to the at least one detector system via a first analytical path and reflecting energy from the second energy source to the at least one detector system via a second analytical path, each of the first analytical path and the second analytical path being less than two feet in length, a length of the first analytical path within the enclosure being less than 10% of a total length of the first analytical path, and a length of the second analytical path within the enclosure being less than 10% of a total length of the second analytical path.

2. The sensor of claim 1 wherein each of the first analytical path and the second analytical path is less than one foot in length.

3. The sensor of claim 1 wherein each of the first analytical path and the second analytical path is less than six inches in length.

4. The sensor of claim 1 wherein the mirror system comprises a first mirror section having a concave shape over at least a portion of a surface thereof and a second mirror section having a concave shape over at least a portion of a surface thereof.

5. The sensor of claim 4 wherein the surface of the first mirror section and the surface of the second mirror section intersect.

6. The sensor of claim 5 wherein the first analytical path and the second analytical paths are of approximately the same length.

7. The sensor of claim 6 wherein the enclosure comprises a window transmissive of infrared energy positioned between each of the first energy source, the second energy source, and the at least one detector system and the mirror system.

8. The sensor of claim 6 wherein the length of the first analytical path within the enclosure is less than 5% of the total length of the first analytical path, and the length of the second analytical path within the enclosure is less than 5% of the total length of the second analytical path.

9. The sensor of claim 5 wherein the first mirror section and the second mirror section are formed on a monolithic base.

10. The sensor of claim 7 wherein the monolithic base is formed from a polymeric material upon which a reflective surface is supported.

11. The sensor of claim 7 wherein the mirror system is supported upon a mirror support that is spaced from the enclosure by at least one extending member in operative connection with the enclosure.

12. The sensor of claim 1 wherein the enclosure comprises a window transmissive of infrared energy positioned between each of the first energy source, the second energy source, and the at least one detector system and the mirror system.

13. The sensor of claim 1 wherein the at least one detector system is a multi-channel detector system including a housing and a beam splitter within housing.

14. The sensor of claim 13 wherein the beam splitter is adapted to split incident infrared light energy into two beams, wherein one beam is directed to a reference channel and another beam is directed to an analytical channel.

15. The sensor of claim 1 wherein the first energy source is modulated at a first frequency and the second energy source is modulated at a second frequency different from the first frequency.

16. The sensor of claim 1 wherein the mirror system comprises a first mirror defining the first analytical path and a second mirror defining the second analytical path, wherein the first mirror is located at a first position and the second mirror is located at a second position different from the first position so that a length of the first analytical path is different from a length of the second analytical path.

17. The sensor of claim 16 wherein each of the first analytical path and the second analytical path is less than one foot in length.

18. The sensor of claim 16 wherein each of the first analytical path and the second analytical path is less than six inches in length.

19. The sensor of claim 18 wherein the enclosure comprises a window transmissive of infrared energy positioned between each of the first energy source, the second energy source, and the at least one detector system and the mirror system.

20. A method of detecting a gas, comprising:

exciting a first energy source positioned within an enclosure such that energy from the first energy source impinges upon a mirror system positioned external to the enclosure and spaced from the enclosure, the mirror system reflecting energy from the first energy source to at least one detector system positioned within the enclosure via a first analytical path, exciting at least a second energy source positioned within an enclosure such that energy from the second energy source impinges upon the mirror system, the mirror system reflecting energy from the second energy source to the at least one detector system via a second analytical path, which is different from the first analytical path, each of the first analytical path and the second analytical path being less than two feet in length, a length of the first analytical path within the enclosure being less than 10% of a total length of the first analytical path, and a length of the second analytical path within the enclosure being less than 10% of a total length of the second analytical path; and determining a concentration of the gas based upon an analytical signal output from the detector system corresponding to the first analytical path and an analytical signal output from the detector system corresponding to the second analytical path.

* * * * *

UNITED STATES PATENT AND TRADEMARK OFFICE
CERTIFICATE OF CORRECTION

PATENT NO.        : 8,785,857 B2  
APPLICATION NO.   : 13/242677  
DATED             : July 22, 2014  
INVENTOR(S)       : Christopher D. Starta et al.

Page 1 of 1

It is certified that error appears in the above-identified patent and that said Letters Patent is hereby corrected as shown below:

In the Claims

Column 8, claim 10, line 63, delete "7" and insert --9--

Column 8, claim 11, line 66, delete "7" and insert --9--

Signed and Sealed this
Twenty-first Day of October, 2014

Michelle K. Lee
*Deputy Director of the United States Patent and Trademark Office*